(12) United States Patent
Ramachandra Iyer et al.

(10) Patent No.: US 11,120,916 B2
(45) Date of Patent: Sep. 14, 2021

(54) METHOD AND A SYSTEM FOR MANAGING TIME-CRITICAL EVENTS ASSOCIATED WITH CRITICAL DEVICES

(71) Applicant: Wipro Limited, Bangalore (IN)

(72) Inventors: Manjunath Ramachandra Iyer, Bangalore (IN); Meenakshi Sundaram Murugeshan, Bangalore (IN)

(73) Assignee: Wipro Limited, Bangalore (IN)

( * ) Notice: Subject to any disclaimer, the term of this patent is extended or adjusted under 35 U.S.C. 154(b) by 183 days.

(21) Appl. No.: 16/276,667

(22) Filed: Feb. 15, 2019

(65) Prior Publication Data
US 2020/0211718 A1    Jul. 2, 2020

(30) Foreign Application Priority Data
Dec. 26, 2018 (IN) .............................. 201841049132

(51) Int. Cl.
*G16H 70/20* (2018.01)
*G16H 40/63* (2018.01)
(Continued)

(52) U.S. Cl.
CPC .............. *G16H 70/20* (2018.01); *G16H 10/60* (2018.01); *G16H 20/10* (2018.01); *G16H 40/63* (2018.01); *G16H 70/40* (2018.01)

(58) Field of Classification Search
CPC .......... G01R 33/5601; G01R 33/56308; G01R 33/281; G01R 33/563; G01R 33/5635;
(Continued)

(56) References Cited

U.S. PATENT DOCUMENTS 8,363,784 B2    1/2013  Sobering et al.
9,478,064 B2    10/2016 Bosscher et al.
(Continued)

FOREIGN PATENT DOCUMENTS

EP    3089664 A1    11/2016
EP    2018108644  *  6/2018

OTHER PUBLICATIONS

Michael A. Bruno, Understanding and Confronting Our Mistakes: The Epidemiology of Error in Radiology and Strategies for Error Reduction, Oct. 14, 2015, RadioGraphics, vol. 35, No. 6, pp. 1-14.*

*Primary Examiner* — Elaine Gort
*Assistant Examiner* — Teresa S Williams
(74) *Attorney, Agent, or Firm* — Finnegan, Henderson, Farabow, Garrett & Dunner, LLP (57) ABSTRACT

The present disclosure discloses method and a critical event managing system for managing time-critical events associated with critical devices. The critical event managing system identifies time-critical events from plurality of events based on predetermined factors related to the plurality of events. The plurality of events is determined from first procedural sequences identified from procedural narration by a practitioner and stored protocol manual. At least one of missed and incorrect events are determined based on comparison between reference and observed values associated with critical devices. A revised execution plan is provided iteratively based on historical data, data provided by practitioner, first procedural sequences, and metadata associated with plurality of parameters. The missed and incorrect events are executed as second procedural sequences based on revised execution plan, thereafter, outcome from execution of first procedural sequences and second procedural sequences is combined in order to manage time-critical events associated with critical devices.

17 Claims, 8 Drawing Sheets

(51) Int. Cl.
*G16H 20/10* (2018.01)
*G16H 10/60* (2018.01)
*G16H 70/40* (2018.01)

(58) Field of Classification Search
CPC .. G01R 33/56316; A61B 6/032; G16H 10/60; G16H 20/40; G16H 70/20; G16H 40/63; G16H 70/40
USPC .......................................................... 705/3
See application file for complete search history.

(56) References Cited

U.S. PATENT DOCUMENTS

| | | | |
|---|---|---|---|
| 10,383,582 B2* | 8/2019 | Miyazawa | A61B 6/4452 |
| 10,957,444 B2* | 3/2021 | Szczykutowicz | G16H 30/40 |
| 2019/0180862 A1* | 6/2019 | Wisser | G16H 80/00 |
| 2019/0370956 A1* | 12/2019 | Jackson | A61B 6/541 |

* cited by examiner

METHOD AND A SYSTEM FOR MANAGING TIME-CRITICAL EVENTS ASSOCIATED WITH CRITICAL DEVICES

TECHNICAL FIELD

The present subject matter is related in general to systems executing time critical activities, more particularly, but not exclusively to a method and system for managing time-critical events associated with critical devices.

BACKGROUND

In recent time, rapid advancement of computer technologies has enabled to use critical systems in real lives. Computer devices and other electronic equipment have undergone huge advancement to improve quality and nature of critical devices. One such example of critical devices is medical devices. Though the medical domain has developed immensely, but still relies on significant human interaction in order to function correctly. For example, there are occasions when a critical or sensitive condition of patient may go unnoticed by a nurse or hospital technician, and not be reported to physician.

Such conditions are prevalent in other critical devices as well. In any time-critical application and devices, it is always vital to observe a user and specified set of tasks continuously and trigger alerts even while minute errors are detected. For example, in the medical domain, almost all tasks are time-bound and critical such as Computed Tomography (CT) scans. Further, the tasks are based on sequence observation, where each sub-task and its sequence need to be evaluated for a type of criticality and accurate outcome results. In addition, this should happen in real-time, considering independently varying parameters misleading human decisions in different directions at different points in time.

In the conventional approach, the critical devices while executing the processes may face problem of critical event mishaps due to real-time misinterpretations by the user and fluctuating parameters associated with the processes. In such case, either re-execution of complete process or a re-plan for the mishaps critical event is required. In the conventional system, factors influencing the re-plan are not known in advance and are not estimated dynamically.

The information disclosed in this background of the disclosure section is only for enhancement of understanding of the general background of the invention and should not be taken as an acknowledgement or any form of suggestion that this information forms the prior art already known to a person skilled in the art.

SUMMARY

In an embodiment, the present disclosure may relate to a method for managing time-critical events associated with critical devices. The method includes identifying one or more time-critical events from a plurality of events based on predetermined factors related to the plurality of events. The plurality of events is determined from a first procedural sequences identified from at least one of procedural narration by a practitioner and stored protocol manual. The method further includes determining at least one of, one or more missed and incorrect events from the identified one or more time-critical events, based on a comparison between reference and observed values associated with a plurality of parameters associated with the critical devices. Further, the method includes providing a revised execution plan for the one or more missed and incorrect events iteratively, based on historical data, data provided by the practitioner, the first procedural sequences, and metadata associated with the plurality of parameters. The one or more missed and incorrect events re executed as second procedural sequences within a predefined time frame based on the revised execution plan. Thereafter, the method includes combining outcome from execution of the first procedural sequences and the second procedural sequences in order to manage the time-critical events associated with critical devices.

In an embodiment, the present disclosure may relate to a critical event managing system for managing time-critical events associated with critical devices. The critical event managing system may include a processor and a memory communicatively coupled to the processor, where the memory stores processor executable instructions, which, on execution, may cause the critical event managing system to identify one or more time-critical events from a plurality of events based on predetermined factors related to the plurality of events. The plurality of events is determined from a first procedural sequences identified from at least one of procedural narration by a practitioner and stored protocol manual. The critical event managing system determines at least one of, one or more missed and incorrect events from the identified one or more time-critical events, based on a comparison between reference and observed values associated with a plurality of parameters associated with the critical devices. Further, the critical event managing system provides a revised execution plan for the one or more missed and incorrect events iteratively, based on historical data, data provided by the practitioner, the first procedural sequences, and metadata associated with the plurality of parameters. The one or more missed and incorrect events are executed as second procedural sequences within a predefined time frame based on the revised execution plan. Thereafter, the critical event managing system combines outcome from execution of the first procedural sequences and the second procedural sequences in order to manage the time-critical events associated with critical devices.

In an embodiment, the present disclosure relates to a non-transitory computer readable medium including instructions stored thereon that when processed by at least one processor may cause a critical event managing system to identify one or more time-critical events from a plurality of events based on predetermined factors related to the plurality of events. The plurality of events is determined from a first procedural sequences identified from at least one of procedural narration by a practitioner and stored protocol manual. The instruction causes the processor to determine at least one of, one or more missed and incorrect events from the identified one or more time-critical events, based on a comparison between reference and observed values associated with a plurality of parameters associated with the critical devices. Further, the instruction causes the processor to provide a revised execution plan for the one or more missed and incorrect events iteratively, based on historical data, data provided by the practitioner, the first procedural sequences, and metadata associated with the plurality of parameters. The one or more missed and incorrect events are executed as second procedural sequences within a predefined time frame based on the revised execution plan. Thereafter, the instruction causes the processor to combine outcome from execution of the first procedural sequences and the second procedural sequences in order to manage the time-critical events associated with critical devices.

The foregoing summary is illustrative only and is not intended to be in any way limiting, in addition to the illustrative aspects, embodiments, and features described above, further aspects, embodiments, and features will become apparent by reference to the drawings and the following detailed description.

BRIEF DESCRIPTION OF THE ACCOMPANYING DRAWINGS

The accompanying drawings, which are incorporated in and constitute a part of this disclosure, illustrate exemplary embodiments and, together with the description, serve to explain the disclosed principles. In the figures, the left-most digit(s) of a reference number identifies the figure in which the reference number first appears. The same numbers are used throughout the figures to reference like features and components. Some embodiments of system and/or methods in accordance with embodiments of the present subject matter are now described, by way of example only, and with reference to the accompanying figures, in which.

It should be appreciated by those skilled in the art that any block diagrams herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and executed by a computer or processor, whether or not such computer or processor is explicitly shown.

DETAILED DESCRIPTION

In the present document, the word "exemplary" is used herein to mean "serving as an example, instance, or illustration," Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however that it is not intended to limit the disclosure to the particular forms disclosed, but on the contrary, the disclosure is to cover all modifications, equivalents, and alternative falling within the scope of the disclosure.

The terms "comprises", "comprising", or any other variations thereof, are intended to cover a non-exclusive inclusion, such that a setup, device or method that comprises a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or method.

In the following detailed description of the embodiments of the disclosure, reference is made to the accompanying drawings that form a part hereof, and in which are shown by way of illustration specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

Embodiments of the present disclosure relates to a method and a critical event managing system for managing time-critical events associated with critical devices. In an embodiment, the critical devices may refer to computer system, electronic or electromechanical system, failure of which may have serious consequences, such as substantial financial losses, substantial environmental damage, injuries or death of human beings. Thus, the critical devices are present in different application domains for example, medical devices, automotive, aerospace, air traffic control and the like. The critical devices perform tasks specific to the device based on a devised execution plan/strategy. Most of the tasks performed by the critical devices are time critical and are very crucial. Sometimes, while performing the tasks, the critical devices may undergo interruptions for some events associated with the tasks due to some unforeseen issue.

Typically, in such conditions, complete task is performed again to obtain desired outcomes. The present disclosure in such situations identifies one or more events which may be at least one of, missed or performed erroneously from the time critical events. A revised execution plan is generated specifically for execution of the at least one or more missed and incorrectly performed events. Thereafter, outcomes from execution of the devised execution plan and the revised execution plan are combined in order to manage the time-critical events associated with the critical devices. The present disclosure aids in adaptive re-planning by considering all possible options and the current progress state without repeating complete procedural sequence.

Figure 1:
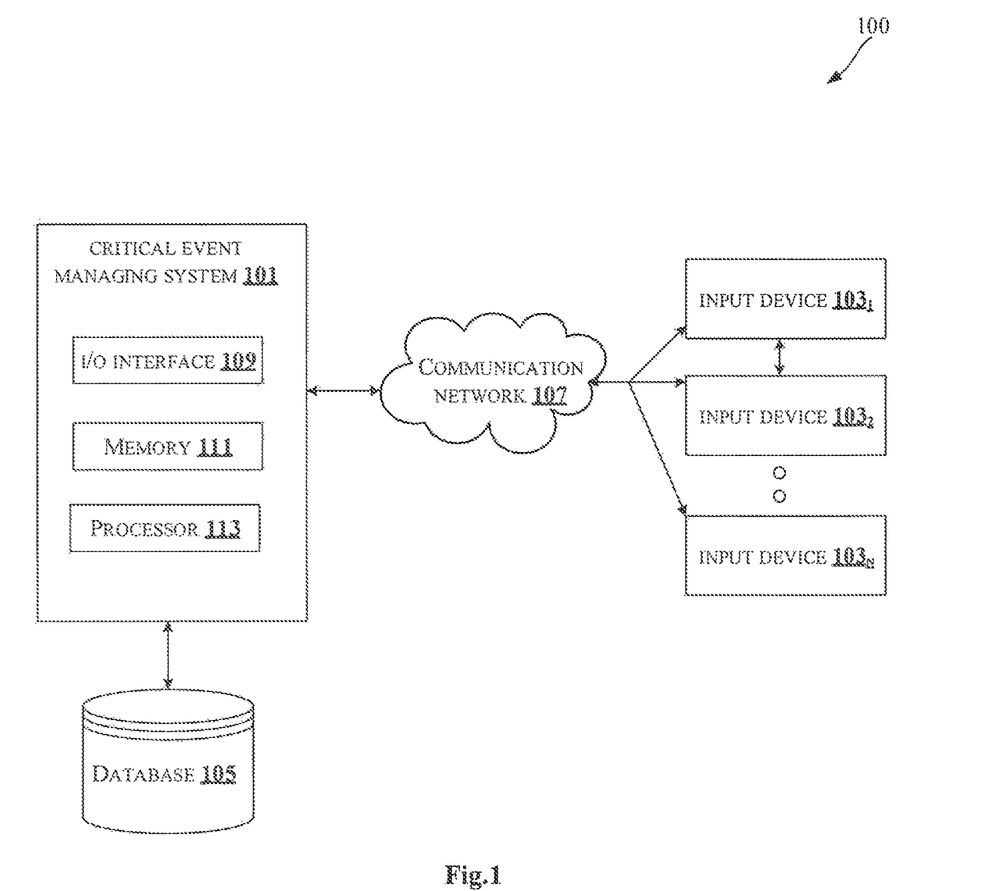
FIG. 1 illustrates an exemplary environment for managing time-critical events associated with critical devices in accordance with some embodiments of the present disclosure.

FIG. 1 illustrates an exemplary environment for managing time-critical events associated with critical devices in accordance with some embodiments of the present disclosure.

As shown in FIG. 1, an environment 100 includes a critical event managing system 101 connected through a communication network 107 to an input device 103i, an input device 1032 . . . and an input device 103N (collectively referred as input devices 103). The critical event managing system 101 may also be connected with a database 105. The input devices 103 may provide procedural narration by a practitioner and stored protocol manual. In an embodiment, the input devices 103 may be any computing devices associated with users, for example, a laptop, a desktop computer, a Personal Digital Assistant (PDA), a notebook, a smartphone, a tablet, a microphone and any other computing devices. A person skilled in the art would understand that the scope of the present disclosure may encompass any other input devices 103, for providing the procedural narration and protocol manual, not mentioned herein explicitly.

In an embodiment, the critical event managing system 101 may exchange data with other components and service providers using the communication network 107. The communication network 107 may include, but is not limited to, a direct interconnection, an e-commerce network, a Peer-to-Peer (P2P) network, Local Area Network (LAN), Wide Area Network (WAN), wireless network (for example, using Wireless Application Protocol), Internet, Wi-Fi and the like.

The critical event managing system 101 may manage time critical events associated with critical devices. In an embodiment, the critical devices may refer to computer systems, electronic or electromechanical systems, failure of which may have serious consequences, such as substantial financial losses, substantial environmental damage, injuries or death of human beings. Thus, the critical devices are present in different application domains for example, medical devices, automotive, aerospace, air traffic control and the like. In one embodiment, the critical event managing system 101 may include, but is not limited to, a laptop, a desktop computer, a Personal Digital Assistant (PDA), a notebook, a smartphone, a tablet, a server, and any other computing devices. A person skilled in the art would understand that, any other devices, not mentioned explicitly, may also be used as the critical event managing system 101 in the present disclosure.

Further, the critical event managing system 101 may include an I/O interface 109, a memory 111 and a processor 113. The I/O interface 109 may be configured to receive the procedural narration, the protocol manual and user inputs from the input devices 103, The procedural narration, the protocol manual and the user inputs received from the I/O interface 109 may be stored in the memory 111, The memory 111 may be communicatively coupled to the processor 113 of critical event managing system 101. The memory 111 may also store processor instructions which may cause the processor 113 to execute the instructions for managing time-critical events associated with critical devices. In an implementation, the critical event managing system 101 may be configured as a standalone device or may be integrated with computing systems.

The critical event managing system 101 on receiving at least one of the procedural narrations by a practitioner and the protocol manual from the input devices 103, determines first procedural sequences associated with a critical device. In an embodiment, the practitioner refers to a person practicing a skilled profession for a specific domain. In an embodiment, the practitioner may provide the procedural narrations offline which may be stored in the database 105. In addition, the database 105 may store the protocol manuals. In one embodiment, the practitioner may narrate the procedural narrations specific to the critical device. The critical event managing system 101 may parse the procedural narrations as and when the practitioner narrates the procedure in any specific language. The parsed procedural narrations and the stored protocol manuals may be used for determining the first procedural sequences for the critical device. Further, from the first procedural sequences, the critical event managing system 101 determines a plurality of events associated with the critical device. In an embodiment, the plurality of events may be determined by identifying one or more actions from the first procedural sequences and associating the one or more actions with a target object upon which the one or more actions is to be performed.

The critical event managing system 101 may identify one or more time-critical events from the plurality of events based on predetermined factors. In an embodiment, the predetermined factors related to the plurality of events include minimum and maximum time gap for a missed event of the plurality of time-critical events, a time duration for executing an event and dependency among plurality of events. Further, as the plurality of events are executed by the critical device, the critical event managing system 101 determines at least one of, one or more missed and incorrect events from the one or more time-critical events based on a comparison between reference and observed values associated with a plurality of parameters of the critical devices.

In an embodiment, the plurality of parameters may be derived from an image of a setup, data from sensors of the critical device and the like. For example, the plurality of parameters in medical domain for a CT angiogram may be breath hold for patient, blood pressure range, pulse and the like. In an embodiment, subsequent events from the first procedural sequences are executed if on comparison a match is identified between the reference and the observed value. In an embodiment, the critical event managing system 101 includes a Natural Language Processing (NLP) unit (not shown explicitly in FIG. 1) for processing inputs from the practitioner. In an embodiment, the critical event managing system 101 queries the practitioner handling the critical device to check if the one or more missing event is critical and depends on any other events in past or if any future event may depend on the one or more missing event.

On determining the one or more missed and incorrect events, the critical event managing system may provide a revised execution plan for the one or more missed and incorrect events iteratively based on historical data, data provided by the practitioner, the first procedural sequences, and metadata associated with the plurality of parameters. However, in case while comparing the reference and the observed values, if a mismatch occurs, the critical event managing system 101 may delay the generation of the revised execution plan for a specific time period within the predefined time frame. The generation of the revised execution plan is delayed checking whether values of the predetermined parameters come to a permitted range, without any changes in values of other predetermined parameters.

In an embodiment, the critical event managing system 101 may discard one or more non-critical activities associated with the one or more missed events in order to execute the one or more missed events within the predefined time frame. The one or more non-critical activities are discarded based on importance of the one or more non-critical activities, smallest time period after which impact of the one or more non-critical activities diminishes, minimization of loss due to discarding and potential reversal of the discarded one or more non-critical activities. A person skilled in the art would understand that, the one or more non-critical activities may be discarded based on any other parameters, not mentioned explicitly herein. In an embodiment, the critical event managing system 101 may alert the practitioner regarding overstepping the predefined time frame, if the revised execution plan cannot be executed within the predefined time frame based on detection of a similar past situation of overstepping the predefined time frame by the practitioner, generation of correct type of caution and learning from response of the practitioner. The one or more missed and incorrect events are executed as second procedural sequences within the predefined time frame based on the revised execution plan. Thereafter, the critical event managing system 101 may combine outcome from execution of the first procedural sequences and the second procedural sequences in order to manage the time-critical events associated with critical devices.

Figure 2A:
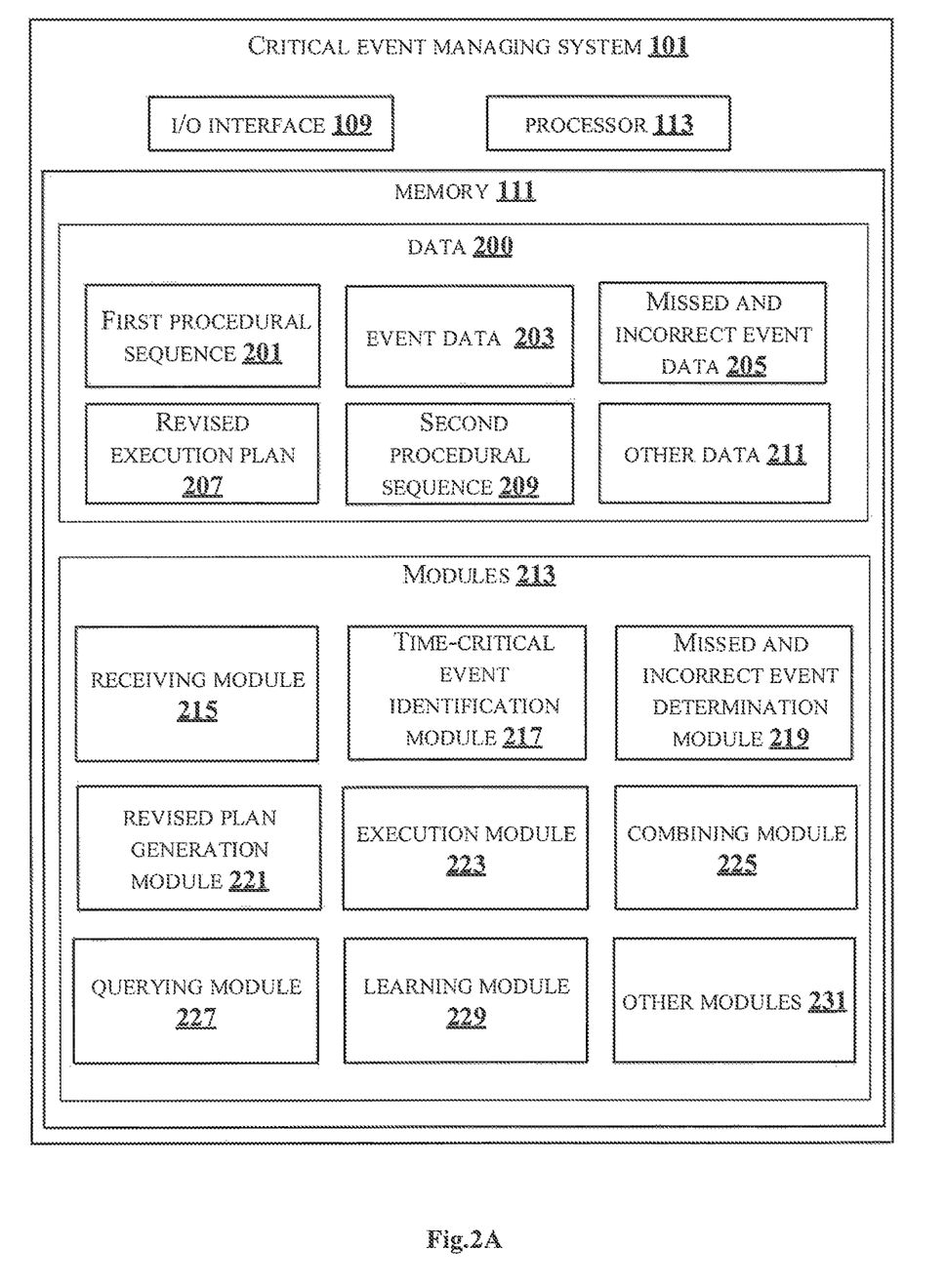
FIG. 2A shows a detailed block diagram of a critical event managing system in accordance with some embodiments of the present disclosure.

FIG. 2A shows a detailed block diagram of a critical event managing system in accordance with some embodiments of the present disclosure.

The critical event managing system 101 may include data 200 and one or more modules 213 which are described herein in detail. In an embodiment, data 200 may be stored within the memory 111. The data 200 may include, for example, first procedural sequence 201, event data 203, missed and incorrect event data 205, revised execution plan 207, second procedural sequence 209, and other data 211.

The first procedural sequence may include sequence of events to be performed by the critical device. The first procedural sequence is determined from at least one of the procedural narrations and the protocol manual received from either the database 105 or from one of the input devices of the plurality of input devices 103. In an embodiment, the first procedural sequence may include protocol as well as detailed actions for each event. For example, the detailed actions may be associated with patients in medical devices, operators of the device and system, i.e., automated steps realized with relays and sensors. For example, table 1 below shows actions associated with patient during CT imaging of coronary artery.

TABLE 1

| Actor | Action |
| --- | --- |
| Radiographer | Inject patient with contrast agent |
| Medical attendant | Put patient in gantry and place gantry in CT machine |
| Patient | Hold breath when advised |
| Radiographer | Capture image |

The event data 203 may include details regarding the plurality of events determined from the first procedural sequences. The event data 203 may also include the one or more time-critical events and stores critical timing information for each of the one or more time-critical events.

The missed and incorrect event data 205 may include details regarding the one or more time-critical events which may be missed or performed incorrectly while performing the first procedural sequence. The missed and incorrect event data 205 may include the minimum and maximum time gap of the one or more missed event of the plurality of time-critical events, the time duration for executing the event and dependency among plurality of events. Further, the missed and incorrect event data 205 may include response from the practitioner regarding criticality of the one or more missed events and dependency of the one or more missed events on any other events in past or if any fixture event may depend on the one or more missing events.

The revised execution plan 207 may include modified execution steps for the one or more missed and incorrect events.

The second procedural sequence 209 may include details associated with the execution of the one or more missed and incorrect events. The details may include one or more activities associated with the one or more missed events for execution, sequence of execution, a time period within with each of the one or more missed events to be executed.

The other data 211 may store data, including temporary data and temporary files, generated by modules 213 for performing the various functions of the critical event managing system 101.

In an embodiment, the data 200 in the memory 111 are processed by the one or more modules 213 present within the memory 111 of the critical event managing system 101. In an embodiment, the one or more modules 213 may be implemented as dedicated units. As used herein, the term module refers to an application specific integrated circuit (ASIC), an electronic circuit, a field-programmable gate arrays (FPGA), Programmable System-on-Chip (PSoC), a combinational logic circuit, and/or other suitable components that provide the described functionality. In some implementations, the one or more modules 213 may be communicatively coupled to the processor 113 for performing one or more functions of the critical event managing system 101. The said modules 213 when configured with the functionality defined in the present disclosure will result in a novel hardware.

In one implementation, the one or more modules 213 may include, but are not limited to a receiving module 215, a time-critical event identification module 217, a missed and incorrect event determination module 219, a revised plan generation module 221, an execution module 223, a combining module 225, a querying module 227 and a learning module 229. The one or more modules 213 may also include other modules 231 to perform various miscellaneous functionalities of the critical event managing system 101. In an embodiment, the other modules 231 may include a first procedural sequence generation module, an NLP module and a correction module.

Figure 2B:
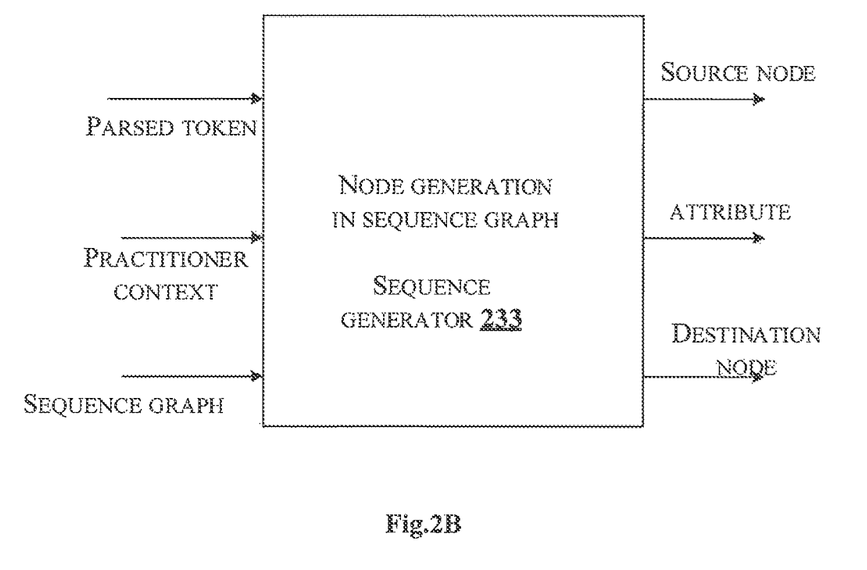
FIG. 2B shows an exemplary representation for determining first procedural sequences in accordance with some embodiments of the present disclosure.

The first procedural sequence generation module may parse the procedural narrations by the practitioner to create a sequence graph 233 as shown in FIG. 2B. In an embodiment, each of the parsed entity is compared with nodes of the sequence graph (empty to start with) to determine if the narration is already a mentioned node of the sequence graph or a new node may be required to be created. For example, if a reference to the node is created, the reference may be linked to node either as a source, if a current event is executed immediately after the node or as a destination, if the current event is to be executed immediately before the node. In an embodiment, if the narration from the practitioner is a part of the metadata of a node or devoid of any actions, which is determined by absence of verbs in the parsed narration, the node may contain one or more named entities or other parts of speech. In an embodiment, if the practitioner narrates continuously about immediately previous event, no event node is created. In an embodiment, description may be classified as an attribute or event based on the presence or absence of relevant action. The attributes are stored in an attribute table of each node.

For example, the user narration, "the bolus looks pale brown" is to be classified as metadata. The narration, "the patient should come in empty stomach to administer the bolus" includes actions like "come" "administer. In an embodiment, patient-specific events are added as metadata. For example, consider the narrations by the practitioner as, "inject contrast agent and get patient on CT gantry, put the gantry in machine and ask patient to hold breath and subsequently take image". In such case, the parsed tokens may include, "put" which is a verb, the gantry and the machine is the named entity. The context may include, "get patient on CT gantry, inject contrast agent". Further, the attributes may be, gantry: CT, whole body, ID, length and the like. The NLP module may parse the procedural narrations and generate tokens, verbs or actions. The NLP module may also generate the queries to the practitioner. The correction module may perform correction for the discarded one or more non-critical activities.

The receiving module 215 may receive at least the procedural narration by the practitioner and the protocol manual for the critical device from the input devices 103. The receiving module 215 may also receive responses from the practitioner for the queries on the one or more missed and incorrect events.

The time-critical event identification module 217 may identify the one or more time-critical events from the plurality of events based on the predetermined factors related to the plurality of events. In an embodiment, the predetermined factors may include the minimum and maximum time gap of the missed event of the plurality of time-critical events, a time duration for executing an event and dependency among plurality of events. In an embodiment, the time-critical event identification module 217 may generate a time graph based on the event data 203 which may indicate critical of the events and dependencies between events.

Figure 2C:
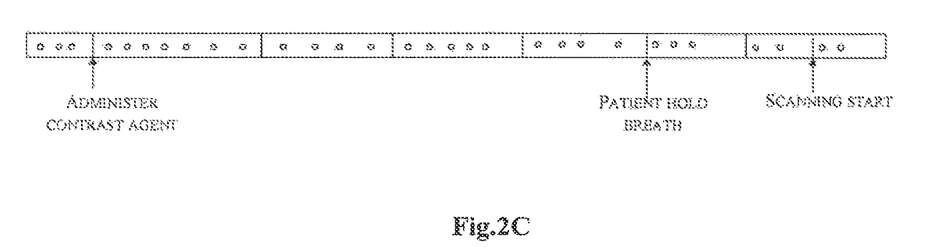
FIG. 2C illustrates an exemplary time graph for CT angiogram in accordance with some embodiment of the present disclosure.
Figure 2D:
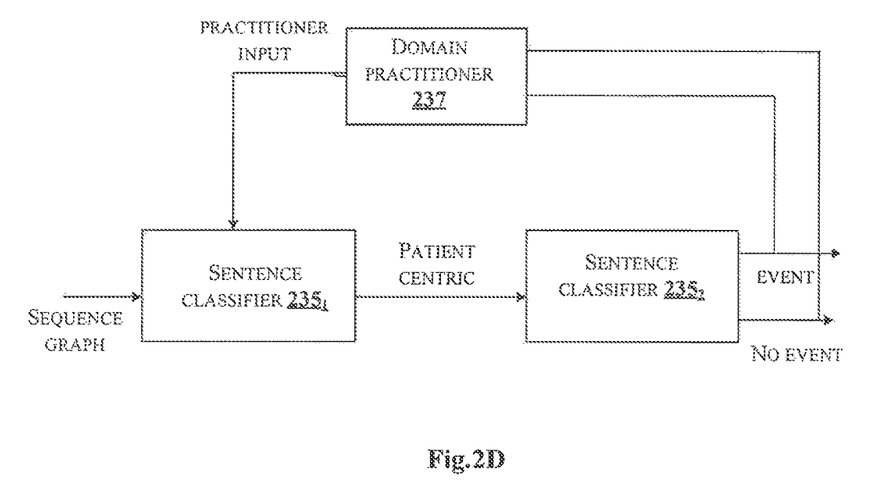
FIG. 2D illustrates an exemplary event filter in accordance with some embodiments of the present disclosure.

FIG. 2C illustrates an exemplary time graph for CT angiogram in accordance with some embodiment of the present disclosure. As shown in FIG. 2C, the time graph for CT angiogram includes events, such that the events are critically depending on each other. While scanning depends on the two events shown in the graph, an event of patient holding breath may not necessarily depend on administering contrast agent event although the sequence is to be followed. The time gap between the administering the contrast and start of the scanning is critical. Thus, the information is stored. FIG. 2D illustrates an exemplary event filter in accordance with some embodiments of the present disclosure. As shown in FIG. 2D, an event filter includes a domain practitioner 237 and two sentence classifiers 2351 and 2352. The event data 203 and the responses from the practitioner may be used as input to the event filter. As shown in FIG. 2D, sentences referring to patient may be parsed by the event filter as the events.

The missed and incorrect event determination module 219 may determine at least one of the one or more missed and incorrect events from the identified one or more time-critical events by comparing the reference and observed values associated with the plurality of parameters associated with the critical devices. In an embodiment, the plurality of parameters may be associated with the image data of the critical device step and the data from the sensors associated with the critical devices. A list of sensor parameters associated with a medical device is shown in table 2 below.

sound which may provide a snapshot of what is expected at end of the event before entering into next event. In the current case, contrast images are for reference. The observed values provide the snapshot of current state. The inference column provides a quick comparison. In the current example, the comparison indicates that no contrast is found in contrast images. Thus, based on the comparison, if the missed and incorrect event determination module 219 identifies a match between reference and observed values, subsequent events from the first procedural sequences are executed.

However, in case of any mismatch, the missed and incorrect event determination module 219 may refer to the controllability and differential value field, as shown in the Table 2. The missed and incorrect event determination module 219 on identifying the mismatch between the reference and observed values waits for a specific time period within the predefined time frame and monitors if the values of the predetermined parameters comes to a permitted range, without any changes in values of other predetermined parameters. For example, if a parameter is not controllable, consider the pulse rate in the Table 2, and if there is a possibility that the pulse rate may come to the permitted range (as indicated in differential value i.e. difference between two consecutive values measured frequently). For example, let the pulse rate be "84" and the differential value is "−1". In such case, the pulse rate may start to stabilize. Thus, in such case, the missed and incorrect event determination module 219 may decide to wait for a specific time, assuming that the contrast is still visible. In an embodiment, a decision to wait may be often subjective and evident from differential value. For example, the differential value may not exist in general for the contrast visibility as it involves frequent imaging with radiation. If an increased concentration in coronary artery is indicated, waiting may be useful, until concentration reaches the maximum.

Figure 2E:
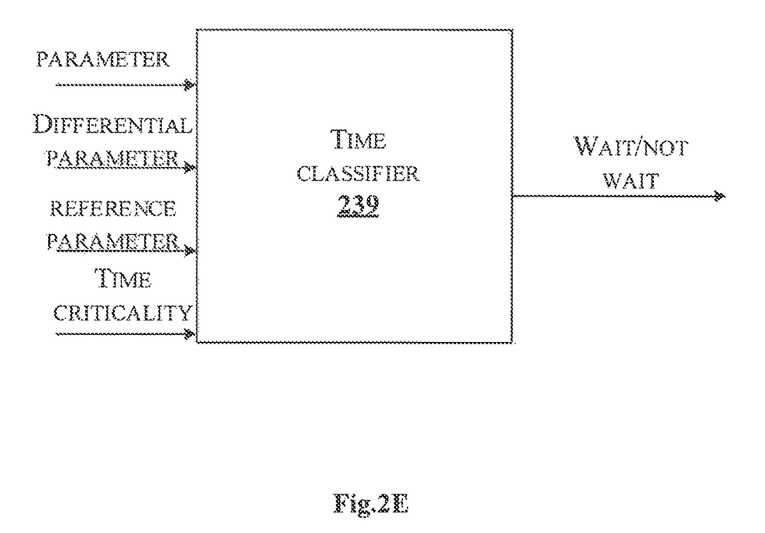
FIG. 2E shows an exemplary time classifier in accordance with some embodiments of the present disclosure.

The missed and incorrect event determination module 219 includes a time classifier as shown in FIG. 2E. FIG. 2E shows a time classifier 239 which helps in the decision to wait or not, in an embodiment, the time classifier may decide based on a rate of change of parameter values, normal range and critical time gaps as input. In an embodiment, the time classifier may also indicate a time to start the subsequent event. In an embodiment, if the match is not possible or not likely to be possible due to the parameters with controllability "yes", it indicates that events are not executed correctly. For example, if the patient breath hold is not performed, reference and observed values may not match. However, the event of patient breath hold may be corrected

TABLE 2

| Parameters | Reference value | Observed value | Inference | Controllability | Differential value |
|---|---|---|---|---|---|
| Patient breath hold | Yes/no | yes | Ok | yes | 0 |
| BP | (160-110)/ (100-60) | 120/80 | Ok | no | −3/+5 |
| Pulse | 60-80 | 70 | Ok | no | +2 |
| Contrast visibility | Contrast.img Contrast1.mpg | Image1.mpg | Empty | yes | Empty/ Contrast2.img |
| ... | | | | | |

The parameters as shown in Table 2 above are an example of CT angiogram. In an embodiment, the reference values include both numerals and images/video, or audio for ultraspontaneously. On the other hand, if the contrast agent is not administered properly, the time classifier may decide not to wait and proceed for revised plan.

The revised plan generation module 221 may generate the revised execution plan iteratively for the one or more missed and incorrect events based on historical data, data provided by the practitioner, the first procedural sequences and metadata associated with the plurality of parameters. While generating the revised execution plan, the revised plan generation module 221 may discard the one or more non-critical activities associated with the one or more missed events to execute the one or more missed events within the predefined time frame. In an embodiment, the one or more non-critical activities are discarded based on importance of the one or more non-critical activities, smallest time period after which impact of the one or more non-critical activities diminishes, minimization of loss due to discarding and potential reversal of the discarded one or more non-critical activities. In an embodiment, the revised plan generation module 221 may prioritize the one or more missed and incorrectly performed events based on high priority event of missed events, next high priority live event, low priority missed event and low priority live event. In an embodiment, the prioritization performed by the revised plan generation module 221 may be stored in the database 105.

Figure 2F:
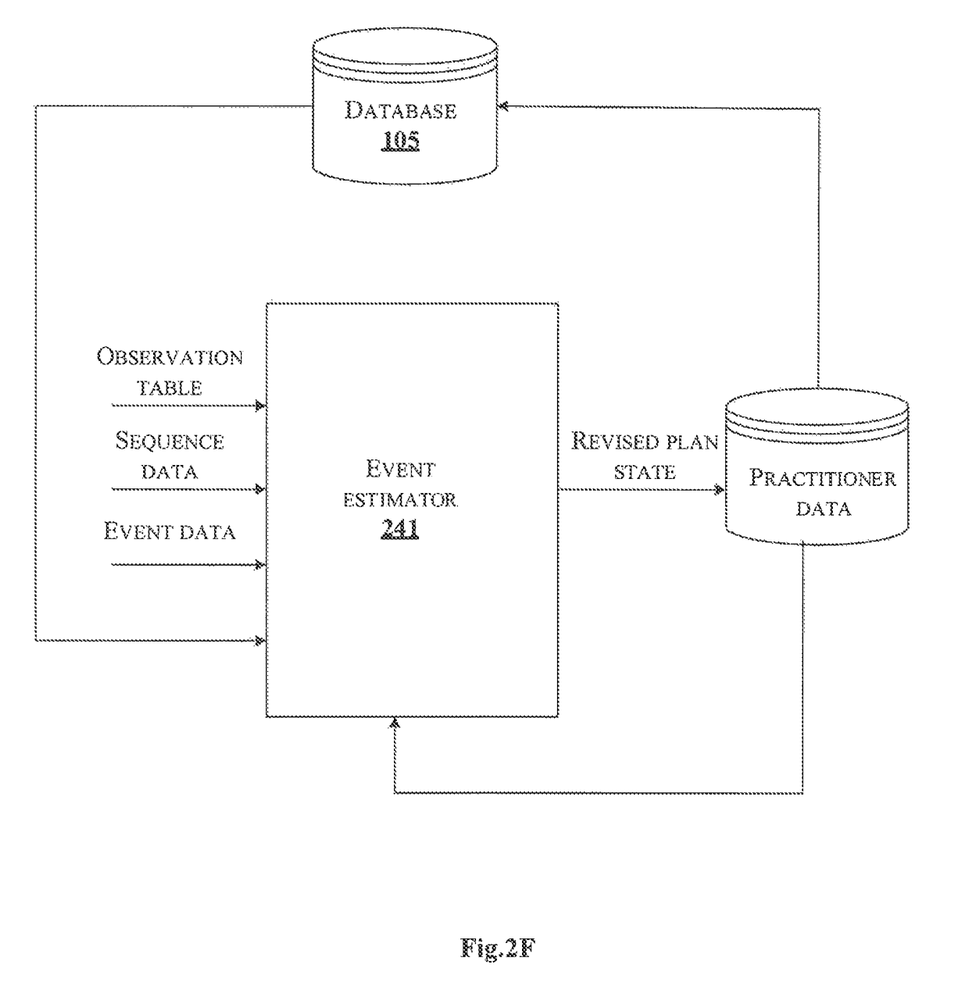
FIG. 2F shows an exemplary event optimizer in accordance with some embodiments of the present disclosure.

The revised plan generation module 221 includes an event optimizer as shown in FIG. 2F for generating the revised execution plan. FIG. 2F shows an exemplary event optimizer which includes an event estimator 241 which takes historical data of handling similar situations for similar critical devices, data provided by the practitioner, the first procedural sequences and metadata associated with the plurality of parameters. In an embodiment, the event optimizer aids to the practitioner narration based on static narrations. In an embodiment, the events identified may be fed to the event optimizer further to optimize dynamic variations in the parameters associated with the identified events.

Figure 2G:
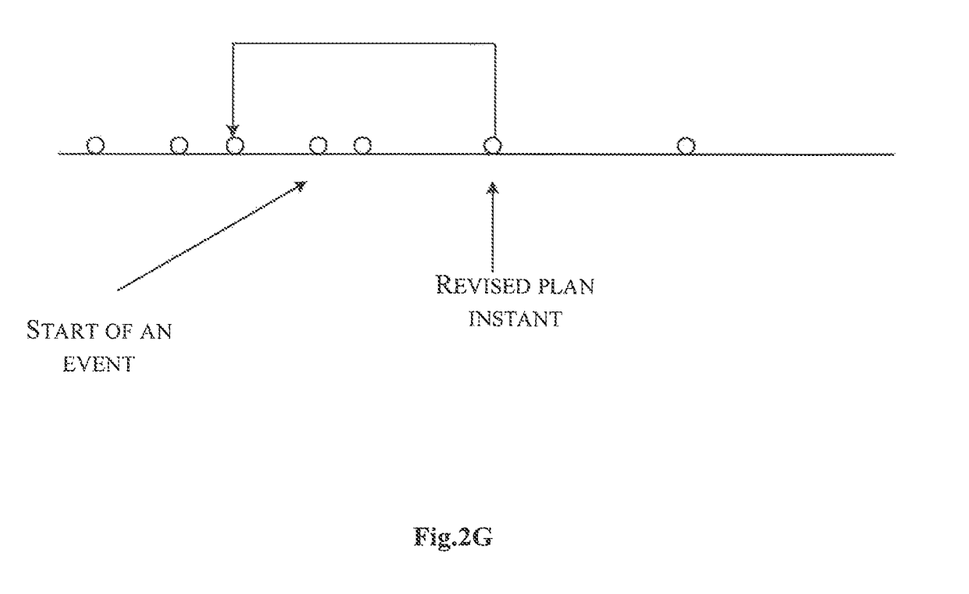
FIG. 2G shows an exemplary embodiment of execution of missed and incorrect events based on revised plan in accordance some embodiments of the present disclosure.

The execution module 223 may execute the one or more missed and incorrect events as second procedural sequences within the predefined time frame based on the revised execution plan. In an embodiment, the execution module 223 may alert the practitioner regarding overstepping the predefined time frame if the revised execution plan cannot be executed within the predefined time frame. The alert may be provided based on the detection of a similar past situation of overstepping the predefined time frame by the practitioner, generation of correct type of caution and learning from response of the practitioner. For example, if the practitioner every time ends up in overstepping the predefined time in spite of cautioning. Thus, the execution module 223 accelerates the execution based on criticality of the missed events. In an embodiment, an iteration state index may be set to indicate how many numbers of looping of revised execution plan is needed. The iteration state index indicates a correct exit for each event. FIG. 2G shows an embodiment of execution of missed and incorrect events based on revised plan. As shown in FIG. 2G, a rollback of few events may happen backward. Thus, re-executing such rollback events.

In an embodiment, the revised plan may avoid rollback, if the rollback is not necessary or if the time period is too close. In this case, the events in the sequence are executed with time catch up, by discarding non-critical events. In an embodiment, the time catch up may be attempted through scaling of time. In one embodiment, the scaling of time may be performed by targeting the catch up time to the immediately next event in the sequence. In case there is a rollback, the rolled hack events may be considered in between. Alternatively, if it is not possible to meet the predefined time period, the execution module 223 may increment the predefined time by "1" and checks the possibility of compressing the event and by how much. Further, checking an impact of deleting a previous event.

The combining module 225 may combine the outcome from execution of the first procedural sequences and the second procedural sequences in order to manage the time-critical events associated with critical devices. In an embodiment, a virtual flow is constructed combining the outcome of the execution of the of the first procedural sequences and the second procedural sequences.

The querying module 227 may transmit queries to the practitioner handling the critical devices to check if the missing event of the plurality of events is critical and depends on any other events in past or any future event depends on the missing event.

The learning module 229 may provide continuous learning based on inputs of the practitioner, previously revised execution plan and time taken by the practitioner to execute the plurality of events.

Figure 3:
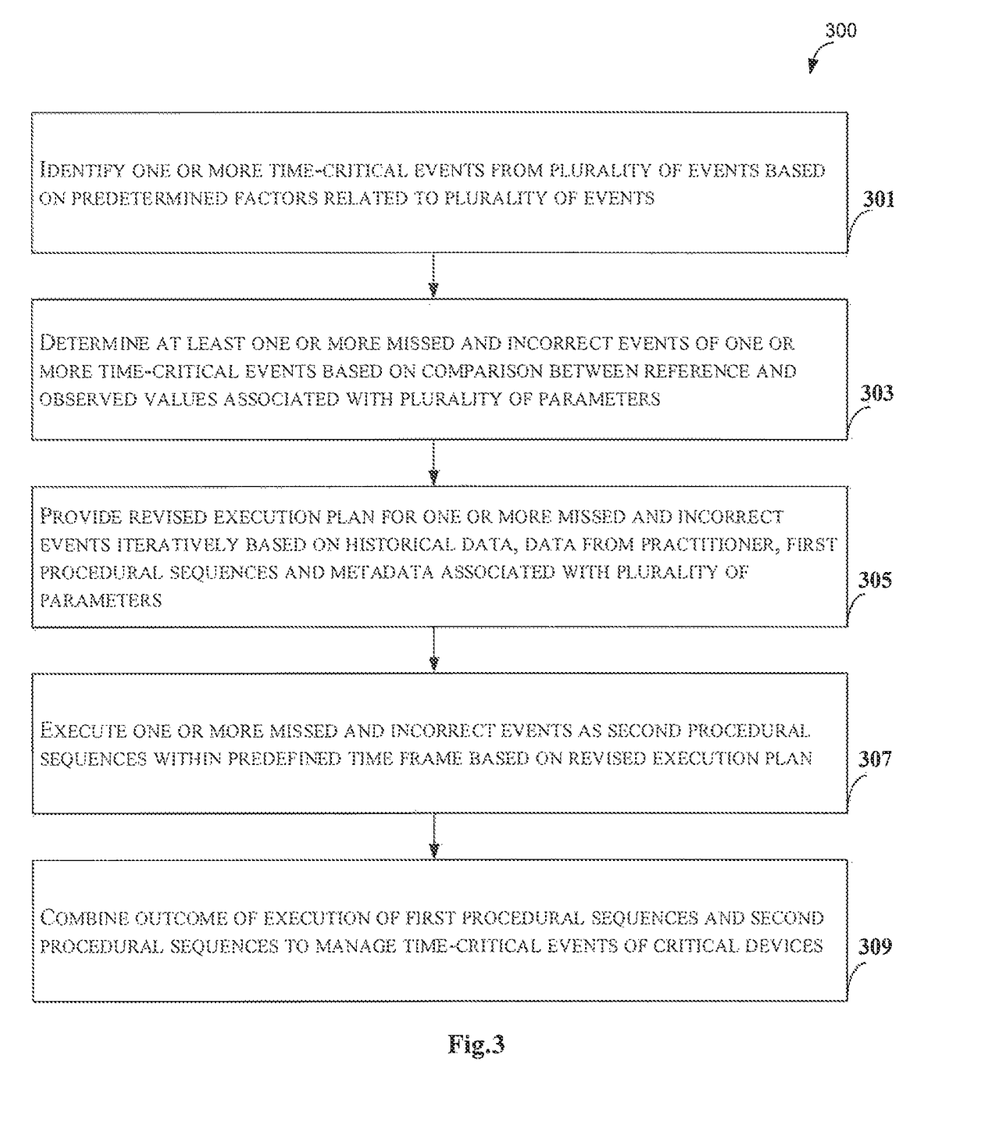
FIG. 3 illustrates a flowchart showing a method for managing time-critical events associated with critical devices in accordance with soiree embodiments of present disclosure.

FIG. 3 illustrates a flowchart showing a method for managing time-critical events associated with critical devices in accordance with some embodiments of present disclosure. As illustrated in FIG. 3, the method 300 includes one or more blocks for managing time-critical events associated with critical devices. The method 300 may be described in the general context of computer executable instructions. Generally, computer executable instructions can include routines, programs, objects, components, data structures, procedures, modules, and functions, which perform particular functions or implement particular abstract data types.

The order in which the method 300 is described is not intended to be construed as a limitation, and any number of the described method blocks can be combined in any order to implement the method, Additionally, individual blocks may be deleted from the methods without departing from the scope of the subject matter described herein. Furthermore, the method can be implemented in any suitable hardware, software, firmware, or combination thereof.

At block 301, the one or more time-critical events from a plurality of events is identified by the time-critical event identification module 217 based on predetermined factors related to the plurality of events. In an embodiment, the plurality of events is determined from the first procedural sequences identified from at least one of procedural narration by the practitioner and the stored protocol manual.

At block 303, at least one of the one or more missed and incorrect events are determined by the missed and incorrect event determination module 219 from the identified one or more time-critical events, based on a comparison between reference and observed values associated with a plurality of parameters associated with the critical devices.

At block 305, the revised execution plan is provided by the revised plan generation module 221 for the one or more missed and incorrect events iteratively, based on historical data, data provided by the practitioner, the first procedural sequences, and metadata associated with the plurality of parameters.

At block 307, the one or more missed and incorrect events are executed by the execution module 223 as the second procedural sequences within the predefined time frame based on the revised execution plan.

At block 309, the outcome from execution of the first procedural sequences and the second procedural sequences is combined by the combining module 225 in order to manage the time-critical events associated with the critical devices.

Figure 4:
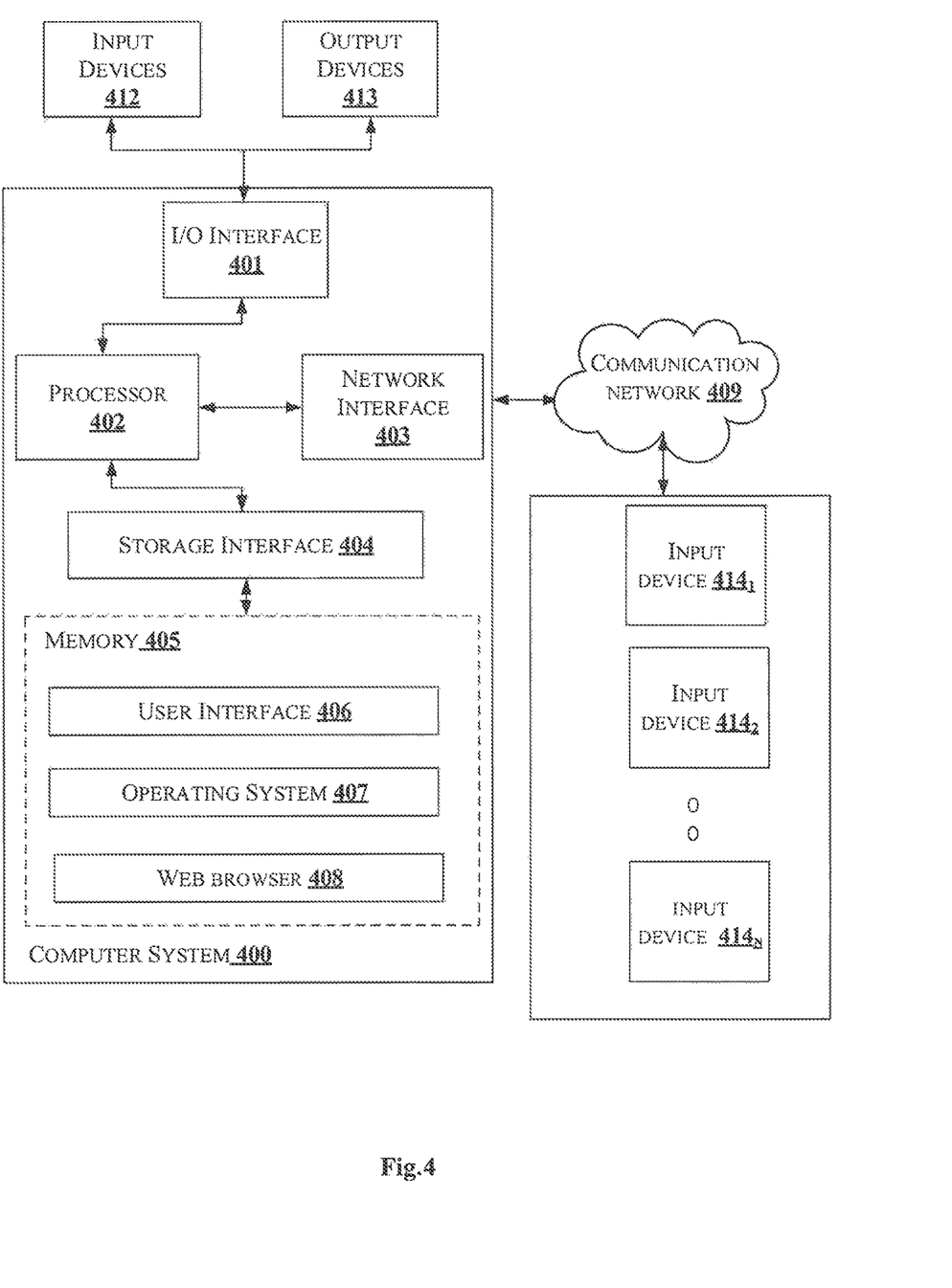
FIG. 4 illustrates a block diagram of an exemplary computer system for implementing embodiments consistent with the present disclosure.

FIG. 4 illustrates a block diagram of an exemplary computer system 400 for implementing embodiments consistent with the present disclosure. In an embodiment, the computer system 400 may be used to implement the critical event managing system 101. The computer system 400 may include a central processing unit ("CPU" or "processor") 402. The processor 402 may include at least one data processor for managing time-critical events associated with critical devices. The processor 402 may include specialized processing units such as, integrated system (bus) controllers, memory management control units, floating point units, graphics processing units, digital signal processing units, etc.

The processor 402 may be disposed in communication with one or more input/output (I/O devices (not shown) via I/O interface 401. The I/O interface 401 may employ communication protocols/methods such as, without limitation, audio, analog, digital, monoaural, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.n/b/g/n/x, Bluetooth, cellular (e.g., code-division multiple access (CDMA), high-speed packet access (HSPA+), global system for mobile communications (GSM), long-term evolution (LTE), WiMax, or the like), etc.

Using the I/O interface 401, the computer system 400 may communicate with one or more I/O devices. For example, the input device may be an antenna, keyboard, mouse, joystick, (infrared) remote control, camera, card reader, fax machine, dangle, biometric reader, microphone, touch screen, touchpad, trackball, stylus, scanner, storage device, transceiver, video device/source, etc. The output device may be a printer, fax machine, video display (e.g., cathode ray tube (CRT), liquid crystal display (LCD), light-emitting diode (LED), plasma, Plasma display panel (PDP), Organic light-emitting diode display (OLED) or the like), audio speaker, etc.

In some embodiments, the computer system 400 consists of the critical event managing system 101. The processor 402 may be disposed in communication with the communication network 409 via a network interface 403. The network interface 403 may communicate with the communication network 409. The network interface 403 may employ connection protocols including, without limitation, direct connect, Ethernet (e.g., twisted pair 10/100/1000 Base T), transmission control protocol/internet protocol (TCP/IP), token ring, IEEE 802.11a/b/g/n/x, etc. The communication network 409 may include, without limitation, a direct interconnection, local area network (LAN), wide area network (WAN), wireless network (e.g., using Wireless Application Protocol), the Internet, etc. Using the network interface 403 and the communication network 409, the computer system 400 may, communicate with an input device $414_1$, an input device $414_2$ . . . and an input device 414N (referred as input devices 414). The network interface 403 may employ connection protocols include, but not limited to, direct connect, Ethernet (e.g., twisted pair 10/100/1000 Base T), transmission control protocol/internet protocol (TCP/IP), token ring, IEEE 802.11a/b/g/n/x, etc.

The communication network 409 includes, but is not limited to, a direct interconnection, an e-commerce network, a peer to peer (P2P) network, local area network (LAN), wide area network (WAN), wireless network (e.g., using Wireless Application Protocol), the Internet, Wi-Fi and such. The first network and the second network may either be a dedicated network or a shared network, which represents an association of the different types of networks that use a variety of protocols, for example, Hypertext Transfer Protocol (HTTP), Transmission Control Protocol/Internet Protocol (TCP/IP), Wireless Application Protocol (WAP), etc., to communicate with each other. Further, the first network and the second network may include a variety of network devices, including routers, bridges, servers, computing devices, storage devices, etc.

In some embodiments, the processor 402 may be disposed in communication with a memory 405 (e.g., RAM, ROM, etc. not shown in FIG. 4) via a storage interface 404. The storage interface 404 may connect to memory 405 including, without limitation, memory drives, removable disc drives, etc., employing connection protocols such as, serial advanced technology attachment (SATA), Integrated Drive Electronics (IDE), IEEE-1394, Universal Serial Bus (USB), fiber channel, Small Computer Systems Interface (SCSI), etc. The memory drives may further include a drum, magnetic disc drive, magneto-optical drive, optical drive, Redundant Array of Independent Discs (RAID), solid-state memory devices, solid-state drives, etc.

The memory 405 may store a collection of program or database components, including, without limitation, user interface 406, an operating system 407 etc. In some embodiments, computer system 400 may store user/application data, such as, the data, variables, records, etc., as described in this disclosure. Such databases may be implemented as fault-tolerant, relational, scalable, secure databases such as Oracle or Sybase.

The operating system 407 may facilitate resource management and operation of the computer system 400. Examples of operating systems include, without limitation, APPLE MACINTOSH® OS X, UNIX®, UNIX-like system distributions (E.G., BERKELEY SOFTWARE DISTRIBUTION™ (BSD), FREEBSD™, NETBSD™, OPENBSD™, etc.), LINUX DISTRIBUTIONS™ (E.G., RED HAT™, UBUNTU™, KUBUNTU™, etc.), IBM™ OS/2, MICROSOFT™ WINDOWS™ (XP™, VISTA™/7/8, 10 etc.), APPLE® IOS™, GOOGLE® ANDROID™, BLACKBERRY™ OS, or the like.

In some embodiments, the computer system 400 may implement a web browser 408 stored program component. The web browser 408 may be a hypertext viewing application, for example MICROSOFT® INTERNET EXPLORER™, GOOGLE® CHROME™, MOZILLA® FIREFOX™, APPLE® SAFARI™, etc. Secure web browsing may be provided using Secure Hypertext Transport Protocol (HTTPS), Secure Sockets Layer (SSL), Transport Layer Security (TLS), etc. Web browsers 408 may utilize facilities such as AJAX™, DHTML®, ADOBE® FLASH™, JAVASCRIPT™, JAVA™, Application Programming interfaces (APIs), etc. In some embodiments, the computer system 400 may implement a mail server stored program component. The mail server may be an Internet mail server such as Microsoft Exchange, or the like. The mail server may utilize facilities such as ASP™, ACTIVEX™, ANSI™ C++/C #MICROSOFT®, .NET™, CGI SCRIPTS™, JAVA™, JAVASCRIPT™, PERL™, PHP™, PYTHON™, WEBOBJECTS™, etc. The mail server may utilize communication protocols such as Internet Message Access Protocol (IMAP), Messaging Application Programming Interface (MAPI), MICROSOFT® exchange, Post Office Protocol (POP), Simple Mail Transfer Protocol (SMTP), or the like. In some embodiments, the computer system 400 may implement a mail client stored program component. The mail client may be a mail viewing application, such as APPLE® MAIL™, MICROSOFT®

ENTOURAGE™, MICROSOFT® OUTLOOK™, MOZILLA® THUNDERBIRD™, etc.

Furthermore, one or more computer-readable storage media may be utilized in implementing embodiments consistent with the present disclosure. A computer-readable storage medium refers to any type of physical memory on which information or data readable by a processor may be stored, Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include Random Access Memory (RAM), Read-Only Memory (ROM), volatile memory, non-volatile memory, hard drives, CD ROMs, DVDs, flash drives, disks, and any other known physical storage media.

An embodiment of the present disclosure indicates a correct time to start a step in the critical device and indicates completeness of a critical event of the critical device.

An embodiment of the present disclosure aids in adaptive re-planning of execution of events for critical devices by considering all possible options and current progress state without repeating complete process.

The described operations may be implemented as a method, system or article of manufacture using standard programming and/or engineering techniques to produce software, firmware, hardware, or any combination thereof. The described operations may be implemented as code maintained in a "non-transitory computer readable medium", where a processor may read and execute the code from the computer readable medium. The processor is at least one of a microprocessor and a processor capable of processing and executing the queries, A non-transitory computer readable medium may include media such as magnetic storage medium (e.g., hard disk drives, floppy disks, tape, etc.), optical storage (CD-ROMs, DVDs, optical disks, etc.), volatile and non-volatile memory devices (e.g., EEPROMs, ROMs, PROMs, RAMs, DRAMs, SRAMs, Flash Memory, firmware, programmable logic, etc.), etc. Further, non-transitory computer-readable media include all computer-readable media except for a transitory. The code implementing the described operations may further be implemented in hardware logic (e.g., an integrated circuit chip, Programmable Gate Array (PGA), Application Specific Integrated Circuit (ASIC), etc.).

Still further, the code implementing the described operations may be implemented in "transmission signals", where transmission signals may propagate through space or through a transmission media, such as, an optical fiber, copper wire, etc. The transmission signals in which the code or logic is encoded may further include a wireless signal, satellite transmission, radio waves, infrared signals, Bluetooth, etc. The transmission signals in which the code or logic is encoded is capable of being transmitted by a transmitting station and received by a receiving station, where the code or logic encoded in the transmission signal may be decoded and stored in hardware or a non-transitory computer readable medium at the receiving and transmitting stations or devices.

An "article of manufacture" includes non-transitory computer readable medium, hardware logic, and/or transmission signals in which code may be implemented. A device in which the code implementing the described embodiments of operations is encoded may include a computer readable medium or hardware logic. Of course, those skilled in the art will recognize that many modifications may be made to this configuration without departing from the scope of the invention, and that the article of manufacture may include suitable information bearing medium known in the art.

The terms "an embodiment", "embodiment". "embodiments", "the embodiment", "the embodiments", "one or more embodiments", "some embodiments", and "one embodiment" mean "one or more (but not all) embodiments of the invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

A description of an embodiment with several components in communication with each other does not imply that all such components are required. On the contrary, a variety of optional components are described to illustrate the wide variety of possible embodiments of the invention.

When a single device or article is described herein, it will be readily apparent that more than one device/article: (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

The illustrated operations of FIG. 3 show certain events occurring in a certain order. In alternative embodiments, certain operations may be performed in a different order, modified or removed. Moreover, steps may be added to the above described logic and still conform to the described embodiments. Further, operations described herein may occur sequentially or certain operations may be processed in parallel. Yet further, operations may be performed by a single processing unit or by distributed processing units.

Finally, the language used in the specification has been principally selected for readability, and instructional purposes, and it may not have been selected to delineate or circumscribe the inventive subject matter. It is therefore intended that the scope of the invention be limited not by this detailed description, but rather by any claims that issue on an application based here on. Accordingly, the disclosure of the embodiments of the invention is intended to be illustrative, but not limiting, of the scope of the invention, which is set forth in the following claims.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

REFERRAL NUMERALS

| Reference number | Description |
|---|---|
| 100 | Environment |
| 101 | Critical event managing system |
| 103 | Input devices |
| 105 | Database |
| 107 | Communication network |
| 109 | I/O interface |
| 111 | Memory |
| 113 | Processor |
| 200 | Data |
| 201 | First procedural sequence |
| 203 | Event data |
| 205 | Missed and incorrect event data |
| 207 | Revised execution plan |
| 209 | Second procedural sequence |
| 211 | Other data |
| 213 | Modules |
| 215 | Receiving module |
| 217 | Time-critical event identification module |
| 219 | Missed and incorrect event determination module |
| 221 | Revised plan generation module |
| 223 | Execution module |
| 225 | Combining module |
| 227 | Querying module |
| 229 | Learning module |
| 231 | Other modules |

What is claimed is:

1. A method for managing time-critical events associated with critical devices, the method comprising:
  identifying, by a critical event managing system, one or more time-critical events from a plurality of events based on predetermined factors related to the plurality, of events, wherein the plurality of events are determined from a first procedural sequences identified from at least one of procedural narration by a practitioner and stored protocol manual;
  determining, by the critical event managing system, at least one of, one or more missed and incorrect events from the identified one or more time-critical events, based on a comparison between reference and observed values associated with a plurality of parameters associated with the critical devices;
  discarding, by the critical event managing system, one or more non-critical activities associated with the one or more missed events to execute the one or more missed events within the predefined time frame, wherein the one or more non-critical activities are discarded based on importance of the one or more non-critical activities, smallest time period after which impact of the one or more non-critical activities diminishes, minimization of loss due to discarding and potential reversal of the discarded one or more non-critical activities;
  providing, by the critical event managing system, a revised execution plan for the one or more missed and incorrect events iteratively, based on historical data, data provided by the practitioner, the first procedural sequences, and metadata associated with the plurality of parameters;
  executing, by the critical event managing system, the one or more missed and incorrect events as second procedural sequences within a predefined time frame based on the revised execution plan; and
  combining, by the critical event managing system, outcome from the execution of the first procedural sequences and the second procedural sequences to manage the time-critical events associated with the critical devices.

2. The method as claimed in claim 1, wherein the predetermined factors comprises one of minimum and maximum time gap of the one or more missed events of the plurality of time-critical events, a time duration for executing an event and dependency among plurality of events.

3. The method as claimed in claim 1, further comprising determining the plurality of events by identifying one or more actions from the procedural narration by the practitioner and the stored protocol manuals and associating the one or more actions with a target object upon which the one or more actions is to be performed.

4. The method as claimed in claim 1 further comprising querying the practitioner handling the critical devices to check if the missed event of the plurality of events is critical and depends on any other events in past.

5. The method as claimed in claim 1, wherein while determining the at least one or more missed and incorrect events, subsequent events from the first procedural sequences are executed on identifying a match between the reference and the observed value on comparison.

6. The method as claimed in claim 1, wherein on identifying a mismatch between the reference and observed values during comparison, generation of the revised execution plan is delayed for a specific time period within the predefined time frame to monitor whether values of the predetermined parameters come to a permitted range, without any changes in values of other predetermined parameters.

7. The method as claimed in claim 1 further comprising alerting the practitioner regarding overstepping the predefined time frame if the revised execution plan cannot be executed within the predefined time frame based on detection of a similar past situation of overstepping the predefined time frame by the practitioner, generation of correct type of caution and learning from response of the practitioner.

8. The method as claimed in claim 1 further comprising performing correction for the discarded one or more non-critical activities.

9. The method as claimed in claim 1 further comprising continuous learning based on inputs of the practitioner, previously revised execution plan and time taken by the practitioner to execute the plurality of events.

10. A critical event managing system for managing time-critical events associated with critical devices, comprising:
  a processor; and
  a memory communicatively coupled to the processor, wherein the memory stores processor instructions, which, on execution, causes the processor to:
    identify one or more time-critical events from a plurality of events based on predetermined factors related to the plurality of events, wherein the plurality of events are determined from a first procedural sequences identified from at least one of procedural narration by a practitioner and stored protocol manual;
    determine at least one of, one or more missed and incorrect events from the identified one or more time-critical events, based on a comparison between reference and observed values associated with a plurality of parameters associated with the critical devices;
    discard one or more non-critical activities associated with the one or more missed events to execute the one or more missed events within the predefined time frame, wherein the one or more non-critical activities are discarded based on importance of the one or more non-critical activities, smallest time period after which impact of the one or more non-critical activities diminishes, minimization of loss due to discarding and potential reversal of the discarded one or more non-critical activities;

provide a revised execution plan for the one or more missed and incorrect events iteratively, based on historical data, data provided by the practitioner, the first procedural sequences, and metadata associated with the plurality of parameters;

execute the one or more missed and incorrect events as second procedural sequences within a predefined time frame based on the revised execution plan; and combine outcome from the execution of the first procedural sequences and the second procedural sequences to manage the time-critical events associated with the critical devices.

11. The critical event managing system as claimed in claim 10, wherein the predetermined factors comprise one of minimum and maximum time gap of the one or more missed events of the plurality of time-critical events, a time duration for executing an event and dependency among plurality of events.

12. The critical event managing system as claimed in claim 10, wherein the processor determines the plurality of events by identifying one or more actions from the procedural narration by the practitioner and the stored protocol manuals and associating the one or more actions with a target object upon which the one or more actions is to be performed.

13. The critical event managing system as claimed in claim 10, wherein the processor queries the practitioner handling the critical devices to check if the missed event of the plurality of events is critical and depends on any other events in past.

14. The critical event managing system as claimed in claim 10, wherein the processor while determining the at least one or more missed and incorrect events, executes subsequent events from the first procedural sequences on identifying a match between the reference and the observed value on comparison.

15. The critical event managing system as claimed in claim 10, wherein the processor on identifying a mismatch between the reference and observed values during comparison, delays generation of the revised execution plan for a specific time period within the predefined time frame to monitor whether values of the predetermined parameters come to a permitted range, without any changes in values of other predetermined parameters.

16. The critical event managing system as claimed in claim 10, wherein the processor alerts the practitioner regarding overstepping the predefined time frame if the revised execution plan cannot be executed within the predefined time frame based on detection of a similar past situation of overstepping the predefined time frame by the practitioner, generation of correct type of caution and learning from response of the practitioner.

17. A non-transitory computer readable medium including instructions stored thereon that when processed by at least one processor cause a critical event managing system to perform operations comprising:

identifying one or more time-critical events from a plurality of events based on predetermined factors related to the plurality of events, wherein the plurality of events is determined from a first procedural sequences identified from at least one of procedural narration by a practitioner and stored protocol manual;

determining at least one of, one or more missed and incorrect events from the identified one or more time-critical events, based on a comparison between reference and observed values associated with a plurality of parameters associated with the critical devices;

discarding one or more non-critical activities associated with the one or more missed events to execute the one or more missed events within the predefined time frame, wherein the one or more non-critical activities are discarded based on importance of the one or more non-critical activities, smallest time period after which impact of the one or more non-critical activities diminishes, minimization of loss due to discarding and potential reversal of the discarded one or more non-critical activities;

providing a revised execution plan for the one or more missed and incorrect events iteratively, based on historical data, data provided by the practitioner, the first procedural sequences, and metadata associated with the plurality of parameters;

executing the one or more missed and incorrect events as second procedural sequences within a predefined time frame based on the revised execution plan; and combining outcome from the execution of the first procedural sequences and the second procedural sequences to manage the time-critical events associated with the critical devices.

* * * * *